United States Patent
Hsu

(10) Patent No.: US 9,886,557 B2
(45) Date of Patent: Feb. 6, 2018

(54) SAFETY ENSURING SYSTEM OF EXERCISE MACHINE AND METHOD OF ENSURING SAFETY WHILE USING AN EXERCISE MACHINE

(71) Applicant: GEE HOO FITEC CORP., New Taipei (TW)

(72) Inventor: Ching-Lu Hsu, Taipei (TW)

(73) Assignee: GEE HOO FITEC CORP., New Taipei (TW)

( * ) Notice: Subject to any disclaimer, the term of this patent is extended or adjusted under 35 U.S.C. 154(b) by 171 days.

(21) Appl. No.: 14/184,108

(22) Filed: Feb. 19, 2014

(65) Prior Publication Data

US 2015/0231447 A1 Aug. 20, 2015

(51) Int. Cl.

| A63B 24/00 | (2006.01) |
| G06F 19/00 | (2011.01) |
| A61B 5/021 | (2006.01) |
| A61B 5/024 | (2006.01) |
| A61B 5/145 | (2006.01) |

(52) U.S. Cl.
CPC .......... *G06F 19/3481* (2013.01); *A61B 5/021* (2013.01); *A61B 5/024* (2013.01); *A61B 5/14542* (2013.01); *A63B 24/00* (2013.01); *A63B 2225/15* (2013.01); *A63B 2230/00* (2013.01)

(58) Field of Classification Search
USPC .................................................... 482/1, 4, 8
See application file for complete search history.

(56) References Cited

U.S. PATENT DOCUMENTS

| 2006/0189440 A1* | 8/2006 | Gravagne | A63B 24/00 482/8 |
| 2013/0253943 A1* | 9/2013 | Lee | G06Q 50/22 705/2 |
| 2014/0129240 A1* | 5/2014 | Zhang | G06Q 50/22 705/2 |

* cited by examiner

*Primary Examiner* — Sundhara Ganesan
*Assistant Examiner* — Shila Jalalzadeh Abyane
(74) *Attorney, Agent, or Firm* — Lynette Wylie; Apex Juris, pllc.

(57) ABSTRACT

A safety ensuring system of exercise machine and a related method includes a physiological detection device and an exercise machine. The physiological detection device is used to detect a physiological state of a human body and save the physiological state. Before a user using the exercise machine, the physiological state of the user is detected by the physiological detection device first. The exercise machine includes a control device and a working device, wherein the control device determines whether the working device is allowed to be used according to the physiological state saved in the physiological detection device. The working device is allowed to be used if the physiological state is normal, and it is prohibited from being used otherwise. Whereby, the user in poor physiological state is prevented from doing exercise, which effectively ensures the safety at using the exercise machine.

10 Claims, 5 Drawing Sheets

SAFETY ENSURING SYSTEM OF EXERCISE MACHINE AND METHOD OF ENSURING SAFETY WHILE USING AN EXERCISE MACHINE

BACKGROUND OF THE INVENTION

1. Technical Field

The present invention relates generally to safety at using an exercise machine, and more particularly, to a safety ensuring system of exercise machines and method of ensuring safety while using an exercise machine.

2. Description of Related Art

Lacking of exercise has become a typical problem for people in the modern world. According to related studies, exercising is good for cardiopulmonary function and blood circulation, which effectively lowers the chances of suffering from chronic diseases. Therefore, those who care about their health would try to make exercise a habit, and using exercise machines is a widely chosen way because it is unaffected by weather conditions.

Moderate amount of exercise is beneficial to health, but it is not easy for people to aware of their physiological state (for example, blood pressure, rhythm of heart, or hemoglobin oxygen saturation) during exercising. And doing exercise under the condition of abnormal physiological state could be harmful, or even leads to sudden death.

Take a gym for example, although there are various kinds of exercise machines provided for their members, and there might be fitness trainers aside, the physiological state of the members is still unlikely to be monitored. Hence, the safety of using exercise machines is not able to be ensured effectively, and the users are actually exposed to some kind of potential hazard.

BRIEF SUMMARY OF THE INVENTION

In view of the above, the primary objective of the present invention is to provide a safety ensuring system of exercise machine, and a method of ensuring safety while using an exercise machine, which could effectively ensure exercise safety.

The present invention provides a safety ensuring system of exercise machine, which includes a physiological detection device and an exercise machine. The physiological detection device has a data storage unit, and is used to detect a physiological state of human body, wherein the physiological state is saved in the data storage unit; the exercise machine includes a control device and a working device, wherein the control device is electrically connected to the physiological detection device, and the control device determines whether the working device is allowed to be used according to the physiological state saved in the data storage unit.

The present invention further provides a method of ensuring safety while using an exercise machine. The method includes the following steps: A. Establish a correspondence between an identity code and a physiological state; B. Input the identity code into the exercise machine; C. Retrieve the physiological state corresponding to the inputted identity code; D. Determine if the exercise machine is allowed to be used or not according to the retrieved physiological state.

Whereby, the present invention determines the permission for a user to use an exercise machine according to his/her physiological state, which prevents the user in poor physiological state from exercising, and therefore the safety of using an exercise machine is effectively ensured.

BRIEF DESCRIPTION OF THE SEVERAL VIEWS OF THE DRAWINGS

The present invention will be best understood by referring to the following detailed description of some illustrative embodiments in conjunction with the accompanying drawings, in which.

DETAILED DESCRIPTION OF THE INVENTION

The detailed description and technical contents of the present invention will be explained with reference to the accompanying drawings. However, the drawings are for illustration only and cannot be used to limit the present invention.

Figure 1:
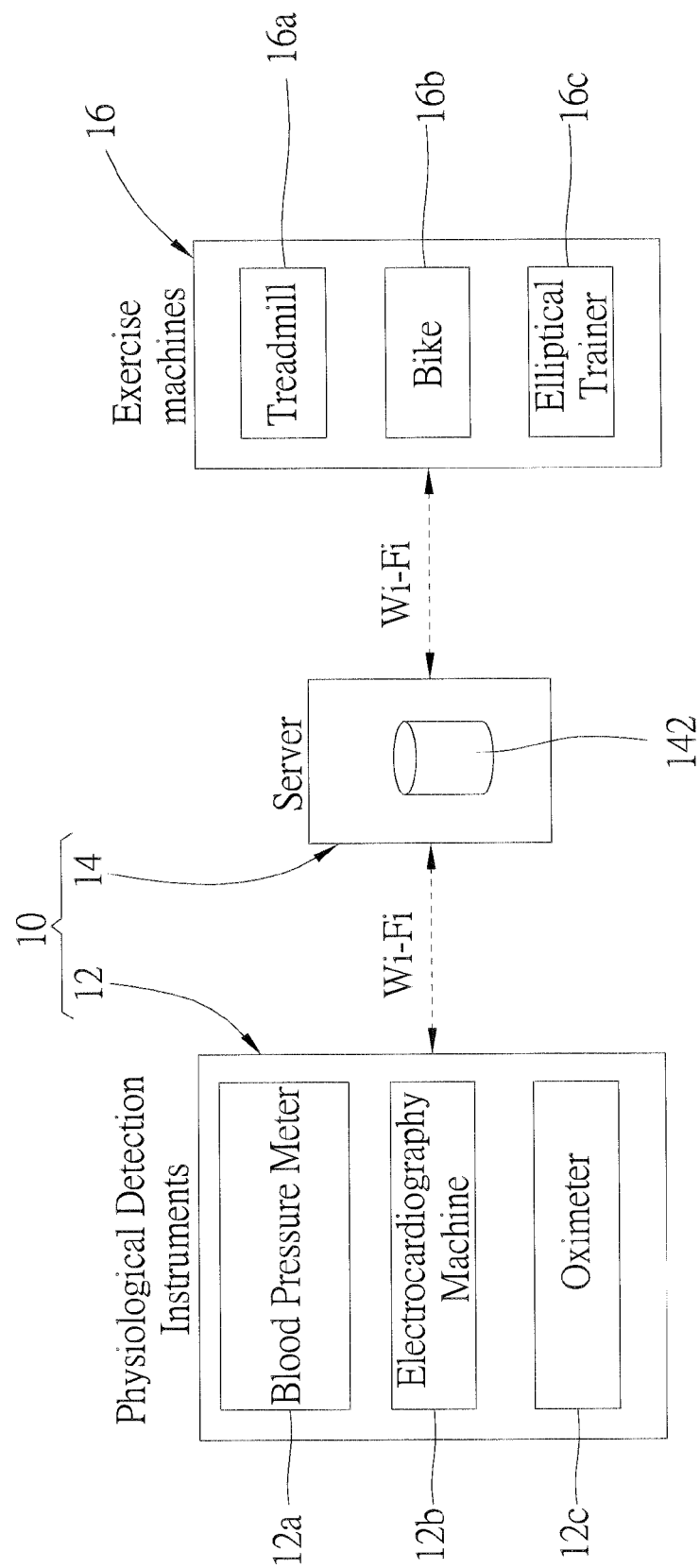
FIG. 1 is a block diagram of the safety ensuring system of a preferred embodiment of the present invention.

As shown in FIG. 1, a safety ensuring system of a preferred embodiment of the present invention includes a physiological detection device 10 and a plurality of exercise machines 16.

In the preferred embodiment, the safety ensuring system is applied in a gym, and each member of the gym is provided with an identifying device, which is a NFC (Near Field Communication) electronic tag in the preferred embodiment. Each NFC tag held by each member is built in with an identity code. Of course, other identifying devices (for example, member cards with barcodes) could be adopted in practice.

Figure 2:
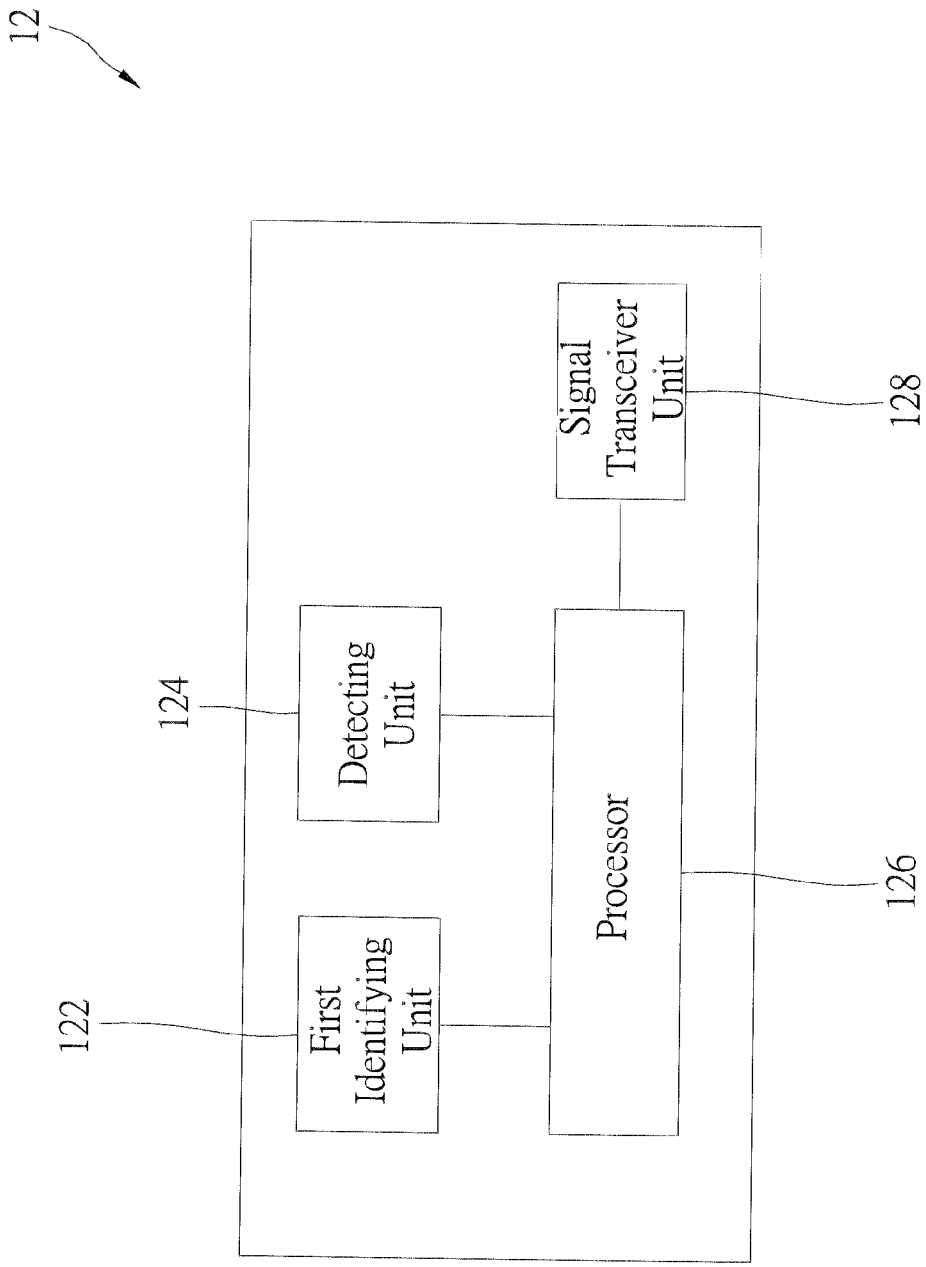
FIG. 2 is a block diagram of the physiological detection instrument of the preferred embodiment of the present invention.

In the preferred embodiment, the physiological detection device 10 includes a plurality of physiological detection instruments 12 and a server 14. The physiological detection instruments 12 include a blood pressure meter 12a, an electrocardiography machine 12b, and an oximeter 12c. Other physiological detection instruments 12 could be adopted in other embodiments, such as body fat meter, non-invasive blood glucose meter, etc. As shown in FIG. 2, each physiological detection instrument 12 includes a first identifying unit 122, a detecting unit 124, a processor 126, and a signal transceiver unit 128. The first identifying unit 122 is a NFC reader, which communicates with the NFC tags held by the members to retrieve identity codes.

The detecting unit 124 detects physiological signals of human body. Take the blood pressure meter 12a for example, the detecting unit 124 detects blood pressure and pulse of human body, and transmits corresponding electrical signals to the processor 126 to generate corresponding physiological signals. Similarly, for the electrocardiography machine 12b, the detecting unit 124 thereof detects bioelectrical potentials of heartbeats, and then sends them to the processor 126. The detecting unit 124 of the oximeter 12c emits specific light onto human body, and receives the intensity of light that goes through human body by a sensor;

after that, the processor 126 processes related measurements to obtain the physiological signals of the hemoglobin oxygen saturation.

The processor 126 sends out the physiological signals, including blood pressure, pulse, bioelectrical potentials of heartbeat, and the hemoglobin oxygen saturation etc., and the identity code identified by the first identifying unit 122 through the signal transceiver unit 128. In the preferred embodiment, the signal transceiver unit 128 transmits data with Wi-Fi signals. Bluetooth, RF, or other wireless transmission means could be selected in other embodiments. In the present embodiment, the physiological detection instruments 12 are medical grade instruments, which could provide accurate detecting results.

The server 14 receives the identity codes and the physiological signals from the signal transceiver units 128 of the physiological detection instruments 12. The server 14 has a data storage unit 142, which saves the identity codes and the corresponding physiological signals. In addition, the server is built in with a comparing program, which analyzes the received physiological signals to generate a physiological state. In the preferred embodiment, the physiological state could be classified as a normal condition, a critical condition, or an abnormal condition by definition. The analysis of the physiological state is based on the standards provided by World Health Organization (WHO) or health authorities at the local area of the gym. In more details, the normal condition indicates that the physiological signals are within a standard range, which is safe for doing exercise normally; the critical condition indicates that the physiological signals are outsight the standard range but not falling into a hazard range, which is suitable for doing exercise with limited intensity; the abnormal condition indicates that the physiological signals are falls into the hazard range, which is not recommended for doing exercise. Take blood pressure for example, the normal condition means that systolic pressure is between 100 and 139 mmHg, and diastolic pressure is between 66 and 90 mmHg; the critical condition means that systolic pressure is between 140 and 179 mmHg, and diastolic pressure is between 91 and 100 mmHg; the abnormal condition means that systolic pressure is higher than 180 mmHg, and diastolic pressure is higher than 101 mmHg. Similarly, for electrocardiography, the condition of the physiological state is determined by analyzing the graph itself; as for blood glucose, the value of blood glucose is the baseline for judgment, and so on.

After analyzing the physiological signals, the server 14 saves the physiological state (as normal, critical, or abnormal condition) which corresponds to the identity code into the data storage unit 142.

Figure 3:
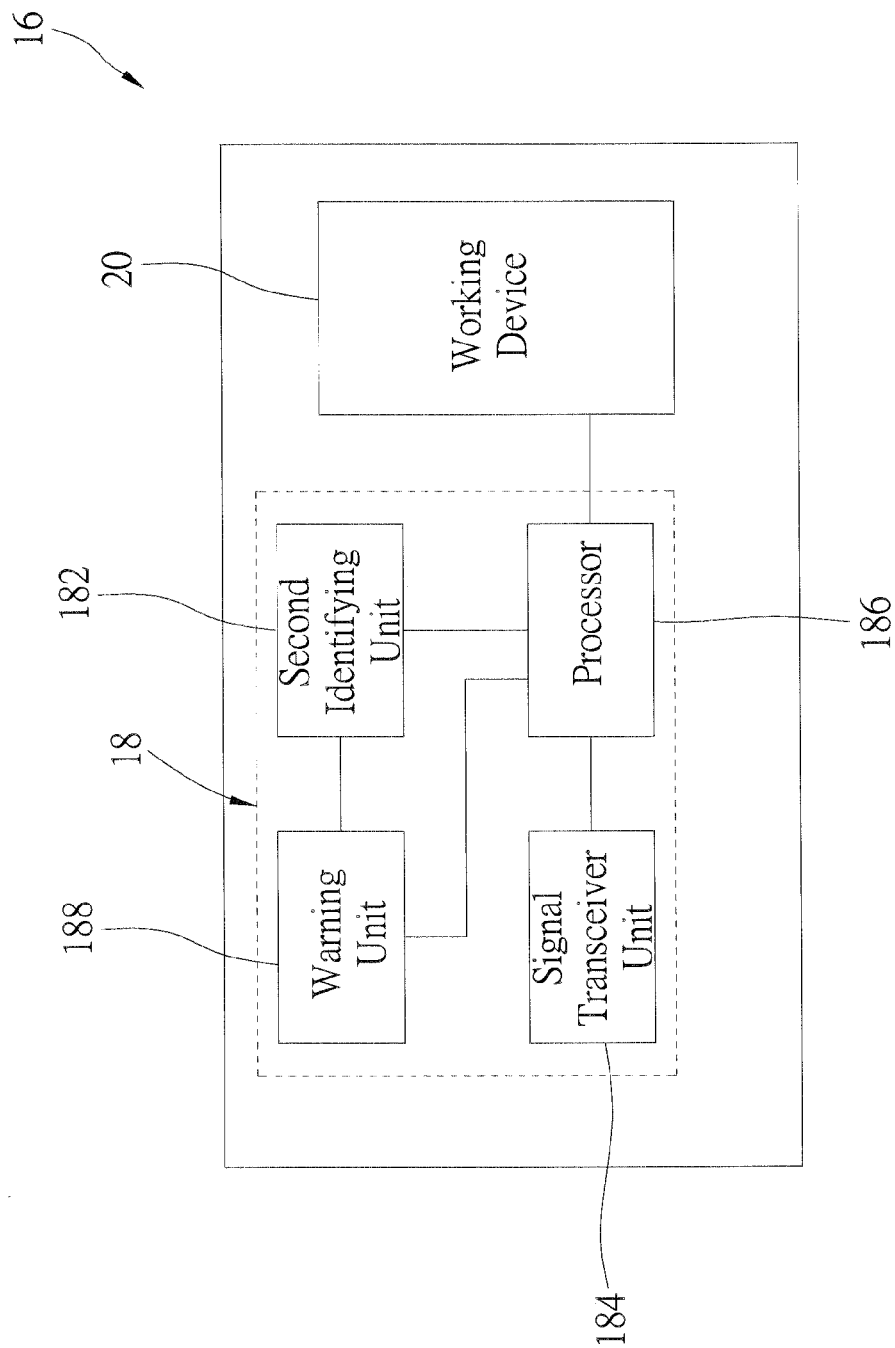
FIG. 3 is a block diagram of the exercise machine of the preferred embodiment of the present invention.

In the preferred embodiment, the exercise machines 16 include a treadmill 16a, a bike 16, and an elliptical trainer 16c. Other exercise machines, such as rowing machine, could be selected in other embodiments. As shown in FIG. 3, each exercise machine 16 includes a control device 18 and a working device 20. The control device 18 includes a second identifying unit 182, a signal transceiver unit 184, a processor 186, and a warning unit 188. The second identifying unit 182 is a NFC reader too, which reads the identity codes of the NFC tags and transmits them to the processor 186. The signal transceiver unit 184 is connected to the server 14 with Wi-Fi signals. In other embodiments, Bluetooth, RF, other wireless transmission means, or cables and the likes of which could be selected for signal transmission between the control device 18 and the server 14. The processor 186 not only turns on and off the working device 20, but also controls the operation intensity of the working device 20 according to the physiological state saved in the data storage unit 142. The processor 186 communicates with the server 14 through the signal transceiver unit 184 to retrieve data in the data storage unit 142. In the preferred embodiment, the warning unit 188 is a speaker, which is controlled by the processor 186 to sound an alarm. In practice, the warning unit 188 could be a stand alone monitor, or a monitor with a speaker.

Figure 4A:
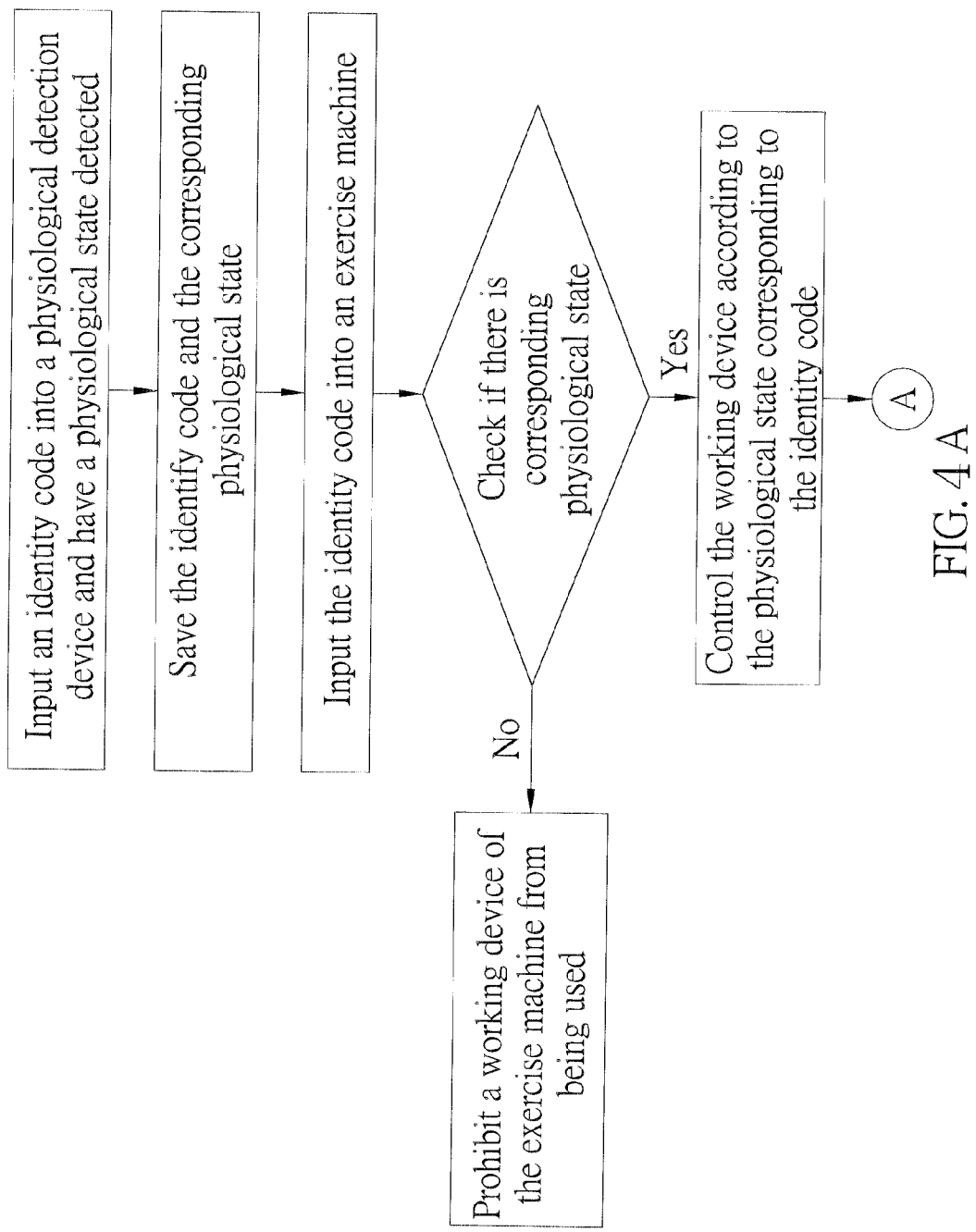
FIG. 4A and FIG. 4B are flow charts of the safety ensuring method of the preferred embodiment of the present invention.
Figure 4B:
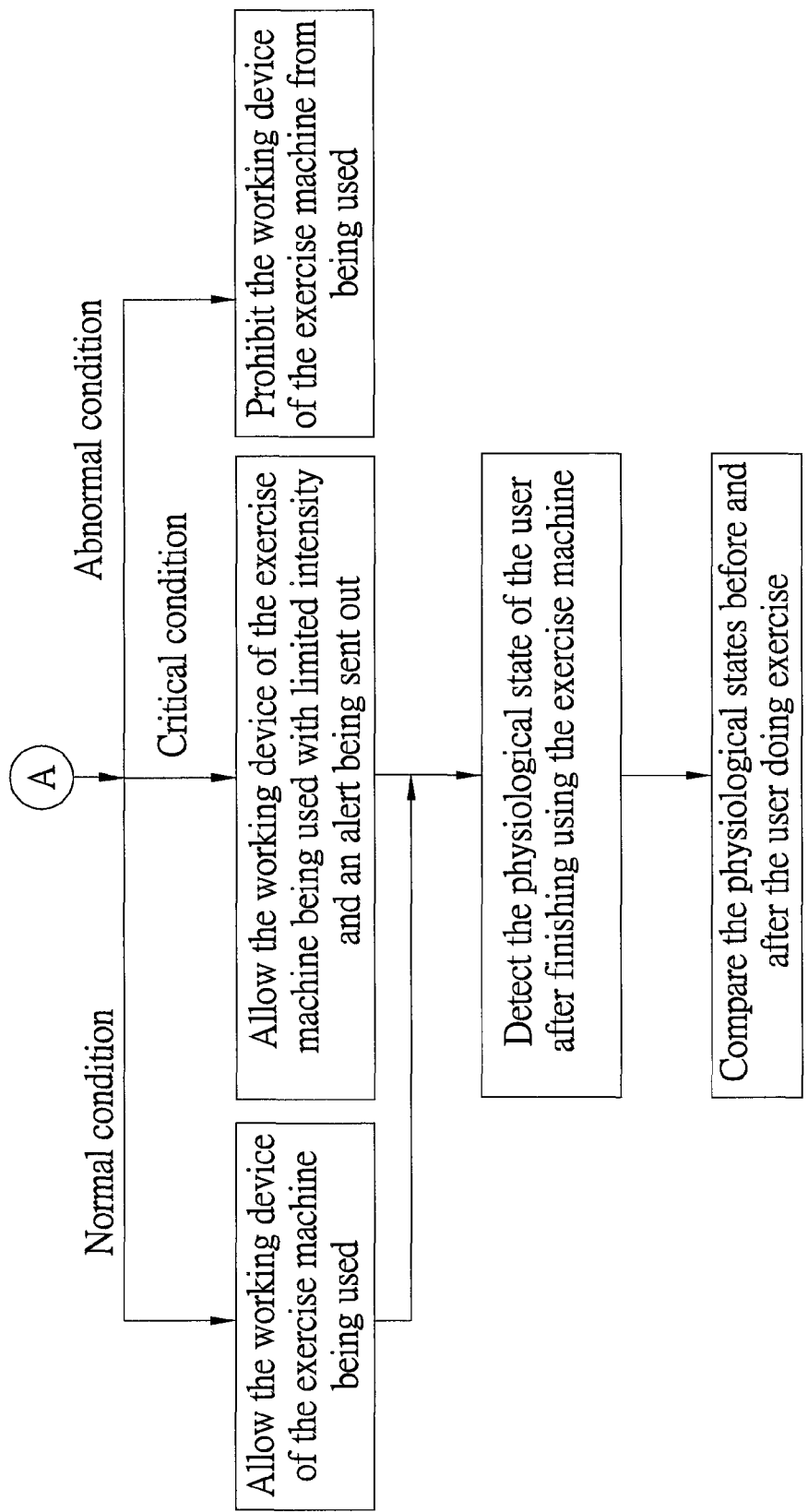

With the aforementioned system, a method of ensuring safety could be applied, as shown in FIGS. 4A and 4B.

First of all, before the user using the exercise machine, the NFC tag held by the user is read by the first identifying unit 122 of the physiological detection instrument 12 to obtain the identity code. Next, the physiological detection instrument 12 detects physiological signals of the user. After detecting, the physiological detection instrument 12 transmits the identity code of the user and the physiological signals to the server 14 to be saved in the data storage unit 142. The server 14 executes the comparing program to analyze the physiological signals, and generates the physiological state (as normal, critical, or abnormal condition) to be saved in the data storage unit 142. Whereby, a correspondence between the identity code and the physiological state is established.

Then, the NFC tag of the user is read by the second identifying unit 182 of any one of the exercise machines 16, which the user intends to use, to obtain the identity code. The processor 186 then communicates with the server 14 through the signal transceiver unit 184 to retrieve the physiological state corresponding to the identity code.

If the processor 186 finds out that the identity code and the corresponding physiological state are not saved in the data storage unit 142, it means that the physiological state of the user has not yet been detected. In such case, the working device 20 is prohibited from being used. Furthermore, the warning unit 188 sends out an alert to request the user to have the physiological state detected.

If the identity code and the corresponding physiological state are found in the data storage unit 142, the processor 186 determined whether the working device 20 is allowed to be used according to the physiological state.

If the physiological state is classified as the normal condition, the working device 20 is allowed to be used, and the user is able to do exercise normally.

If the physiological state is classified as the critical condition, the working device 20 is allowed to be used with limited intensity. In this way, the user could only exercise moderately for safety. In addition, the warning unit 188 sends out another alert to remind the user not to do exercise too fiercely. For example, if the exercise machine 16 used by the user is the treadmill 16a, then an endless track of the working device 20 of the treadmill 16a is restricted from rotating higher than 4 km per hour, which allows the user to walk slowly on it.

If the physiological state is classified as the abnormal condition, the working device 20 is prohibited from being used, and the warning unit 188 sends out another alert to remind the user that he/she is not suitable for exercising right now, which ensures the safety of the user.

After doing exercise with any one of the exercise machines 16, the user could be reminded by the warning unit 188 to have the physiological state detected again. After detecting, the physiological signals and the physiological state at this time point is saved by the server 14 for comparison purpose. If the physiological state of the user is classified as the abnormal condition after doing exercise, the user could realize that he has to take certain appropriate actions, such as going to hospital or so. In practice, the server 14 could transmit comparing results back to the physiological detection instrument 12 to be displayed there or on another monitor instead. Whereby, the user is able to know his/her physiological states before and after doing exercise.

In summary, the safety ensuring system and the method of the present invention could determine the permissions for using exercise machines according to the physiological state of the user, which effectively prevents the user in poor physiological state from doing exercise, and increases the safety at using exercise machines.

It must be pointed out that the embodiments described above are only some preferred embodiments of the present invention. All equivalent structures and methods which employ the concepts disclosed in this specification and the appended claims should fall within the scope of the present invention.

What is claimed is:

1. A computer implemented method of ensuring safety for using an exercise machine, comprising the steps of:
   a) obtaining, before using an exercise machine, an identity code of a user;
   b) detecting physiological signals of the user;
   c) transmitting the identity code and the physiological signals to a server;
   d) generating a physiological state of the user and establishing a correspondence between an identity code of the user and the physiological state of the user; wherein the physiological state is classified as a normal condition, an abnormal condition, or a critical condition;
   e) inputting the identity code of the user into the exercise machine;
   f) retrieving the physiological state corresponding to the inputted identity code of the user;
   g) determining, based on the retrieved physiological state of the user, if the exercise machine is allowed to be activated and used by the user or not;
   wherein, responsive to the determination:
      i. allowing the exercise machine to be activated and used by the user, when the retrieved physiological state of the user is classified as the normal condition;
      ii. prohibiting the exercise machine from being activated and used by the user, when the retrieved physiological state of the user is classified as the abnormal condition; and
      iii. allowing the exercise machine to be activated and used by the user with limited intensity and sending out an alert, when the retrieved physiological state of the user is classified as the critical condition.

2. The computer implemented method of claim 1, wherein the step of obtaining, before using an exercise machine, an identity code of a user is done by inputting the identity code of the user into a physiological detection device; wherein the physiological detection device detects the physiological signals of the user and establishes the correspondence between the inputted identity code of the user and the detected physiological signals of the user.

3. The computer implemented method of claim 2, wherein the physiological state is obtained by analyzing the detected physiological signals of the user.

4. The computer implemented method of claim 3, wherein the physiological signals include blood pressure, hemoglobin oxygen saturation, or electrocardiography.

5. The computer implemented method of claim 1, wherein in step f), if the physiological state is not retrievable, the exercise machine is prohibited from being activated and used.

6. The computer implemented method of claim 1, further comprising the steps of determining the user's physiological state after the user finishes using the exercise machine.

7. A safety ensuring system for an exercise machine, comprising:
   a physiological detection device having a data storage unit; and
   an exercise machine including a control device and a working device; the control device being electrically connected to the physiological detection device,
   wherein, before the exercise machine is used, the physiological detection device determines a physiological state of a user and saves the physiological state of the user in the data storage unit, wherein the physiological state is classified as a normal condition, an abnormal condition, or a critical condition;
   wherein, the control device retrieves the physiological state of the user from the data storage unit and determines whether the working device is allowed to be activated and used by the user or not, according to the retrieved physiological state of the user;
   wherein, if the retrieved physiological state is classified as the normal condition, the control device controls the working device to be allowed to be activated and used by the user;
   wherein, if the retrieved physiological state is classified as the abnormal condition, the control device controls the working device to be prohibited from being activated and used by the user; and
   wherein, if the retrieved physiological state is classified as the critical condition, an alert is sent out by a warning unit and the control device controls the working device to be allowed to be activated and used by the user with limited intensity.

8. The safety ensuring system of claim 7, wherein the physiological detection device comprises:
   a physiological detection instrument, wherein the physiological detection instrument detects physiological signals of the user; and
   a server having the data storage unit, wherein the server is connected to the control device and generates the physiological state of the user by analyzing the detected physiological signals of the user.

9. The safety ensuring system of claim 8, wherein the physiological signals include blood pressure, hemoglobin oxygen saturation, or electrocardiography.

10. The safety ensuring system of claim 7, wherein the physiological detection device includes a first identifying unit to receive an identity code of the user, the identity code of the user and the physiological state corresponding to the identity code of the user are saved in the data storage unit; and the control device includes a second identifying unit to receive the identity code of the user, wherein the control device retrieves the physiological state associated with the received identity code of the user from the data storage unit.

* * * * *